United States Patent

Shachat et al.

[11] Patent Number: 6,069,275
[45] Date of Patent: May 30, 2000

[54] MONOMERS AND POLYMERS AND LATICES THEREFROM

[75] Inventors: Norman Shachat, Yardley, Pa.; Zenyk Kosarych, New Egypt, N.J.

[73] Assignee: Rhodia Inc., Cranbury, N.J.

[21] Appl. No.: 09/014,552

[22] Filed: Jan. 28, 1998

[51] Int. Cl.$^7$ ........................ C07C 269/00; C07C 273/00; C08F 226/06
[52] U.S. Cl. ........................ 564/105; 564/32; 526/259; 526/288
[58] Field of Search ........................ 564/1.5, 32; 526/259

[56] References Cited

U.S. PATENT DOCUMENTS

| | | | |
|---|---|---|---|
| 2,613,212 | 10/1952 | Hurwitz et al. | 260/309.7 |
| 3,356,655 | 12/1967 | Sekmakas | 260/78.5 |
| 3,509,085 | 4/1970 | Sekmakas | 260/29.6 |
| 4,111,877 | 9/1978 | Dixon et al. | 260/29.6 |
| 4,487,940 | 12/1984 | Sekmakas et al. | 548/320 |
| 4,526,915 | 7/1985 | Sekmakas et al. | 524/83 |
| 4,730,045 | 3/1988 | Sekmakas et al. | 544/318 |
| 5,371,148 | 12/1994 | Taylor | 525/293 |
| 5,612,441 | 3/1997 | Dochniak | 528/289 |

OTHER PUBLICATIONS

G. Pohlein, "Emulsion Polymerization", *Encyclopedia of Polymer Science and Engineering*, vol. 6, p. 1 (John Wiley & Sons, Inc., N. Y., N. Y., 1986).

J. Lowell, "Coatings", *Encyclopedia of Polymer Science and Engineering*, vol. 3, pp. 650–652 (John Wiley & Sons, Inc., N. Y., N. Y., 1985).

*Primary Examiner*—Tae Yoon
*Attorney, Agent, or Firm*—John Daniel Wood

[57] ABSTRACT

A novel monomer composition for promoting wet adhesion of latex polymers for paints is provided. The composition consists essentially of a monomer having the formula:

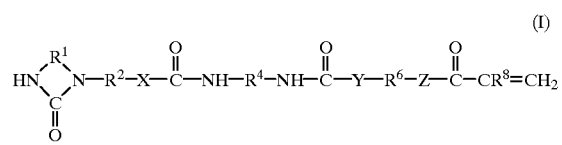

(I)

The preferred monomer is derived from the reaction of hydroxyethyl methacrylate with isophorone diisocyanate followed by reaction of the monourethane product the N-aminoethyl ethylene urea. The monomer is preferably copolymerized in an emulsion polymerization with acrylic and/or vinyl monomers.

34 Claims, No Drawings

MONOMERS AND POLYMERS AND LATICES THEREFROM

FIELD OF THE INVENTION

This invention relates to novel monomers useful for promoting the wet adhesion of latex coatings, to latices and paints prepared therewith and to related methods.

BACKGROUND OF THE INVENTION

The use of water-based emulsion polymer systems as protective and decorative coatings for many types of surfaces has become widespread. The so-called latex paint is commonly used by individuals in homes and industrially. While oil-based systems are known to retain their adhesive properties under wet or humid conditions, a characteristic called "wet adhesion," the tendency of many water-based coating to lose their adhesive properties when wet has limited the usefulness of such coatings. This is particularly true for paints based on vinyl-acrylic or all acrylic latices which otherwise are attractive as paint vehicles.

Paints intended for outdoor use are frequently exposed to moisture and humidity, as are paints used on interior surfaces in wet or humid atmospheres, such as in bathrooms and kitchens. Good wet adhesion is an important attribute of paints applied to those surfaces and others where resistance to water and abrasion is important, as where paints are exposed to washing or scrubbing, and where water-based paints are applied to glossy surfaces. In these situations, the need for improved wet adhesion of aqueous emulsion polymer systems is particularly great.

The art has recognized the problem of loss of adhesive properties in latex paints when wet, and a variety of additives to latex systems to improve wet adhesion has been proposed. For example, U.S. Pat. No. 3,356,655, issued on Dec. 5, 1967, and U.S. Pat. No. 3,509,085, issued on Apr. 28, 1970, disclose a number of ethylenically unsaturated hydroxy-functional amines which are said to be useful in improving adhesion and water resistance of latex paints. In addition, U.S. Pat. No. 4,111,877, issued on Sep. 5, 1978, discloses certain imidazolidinone derivatives which are said to improve the adhesive properties of latex paint.

It has now been found that latex-containing surface coatings and coating compositions having excellent wet adhesion properties can be produced by including in the monomer system one or a mixture of novel polymerizable monomers. In particular, the new compounds of this invention have been found to be especially useful in water-based latex-containing paints and can also be employed as comonomers in solution polymers.

U.S. Pat. Nos. 4,487,940 and 4,526,915 (Sekmakas et al.) disclose an acrylate or methacrylate functional copolymerizable monomer which serves to improve the adhesion of emulsion polymers is disclosed. This monomer is the adduct formed by reacting an aminoalkyl alkylene urea with about 0.9 up to about 1.5 molar proportions of a saturated monoepoxide to consume most or all of one of the two amino hydrogen atoms available, and then reacting with about 0.8 up to about 2.0 molar proportions of a monoisocyanate having a single acrylate or methacrylate group in the presence of at least 0.02%, based on the total weight of the reactants present, of an inhibitor, such as hydroquinone or phenothiazine, which retards the free-radical polymerization of ethylenic unsaturation.

SUMMARY OF THE INVENTION

This invention relates to a composition of matter consisting essentially of a monomer having the formula:

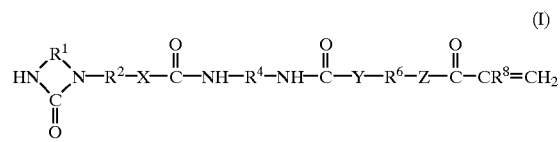

wherein:

$R^1$ is alkylene having about 2 or 3 carbon atoms, preferably 2 carbon atoms;

$R^2$ is alkylene having about 2 to about 10 carbon atoms, preferably 2 or 3 carbon atoms;

X is oxygen, sulfur, or $NR^3$ wherein $R^3$ is hydrogen, alkyl, substituted alkyl, alicyclic, substituted alicyclic, aryl, substituted aryl, heteroalkyl, heterocyclic, preferably X is NH;

$R^4$ has the structure of the residue of an alicylic diisocyanate wherein the isocyanate groups have reactivites that differ one from another, preferably $R^4$ has the structure of the residue of an alicylic diisocyanate wherein one or more alkyl groups pendant to an alicylic ring provide greater steric hindrance to one isocyanate group than the other isocyanate group, e.g. wherein $R^4$ has the structure of the residue of isophorone diisocyanate;

Y is oxygen, sulfur, or $NR^5$ wherein $R^5$ is hydrogen, alkyl, substituted alkyl, alicyclic, substituted alicyclic, aryl, substituted aryl, heteroalkyl, or heterocyclic, Y is preferably oxygen;

$R^6$ is alkylene, arylene, aralkylene, alkarylene, or heteroalkylene, preferably ethylene;

Z is oxygen, sulfur, or $NR^7$ wherein $R^7$ is hydrogen, alkyl, substituted alkyl, alicyclic, substituted alicyclic, aryl, substituted aryl, heteroalkyl, or heterocyclic, Z is preferably oxygen; and $R^8$ is hydrogen or methyl, preferably methyl.

This invention also relates to a method of making a monomer composition as described above wherein a diisocyanate of formula OCN—$R^4$—NCO is reacted with an ethylenically unsaturated compound of formula HY—$R^6$—Z—C(O)—$CR^8$=$CH_2$ and the product thereof is reacted with a compound of formula (II):

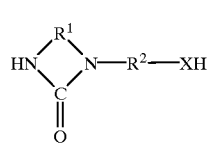

This invention also relates to polymers and latices prepared from the monomers of this invention and to methods of making latices comprising blending latices, and the use of latices in making water-based paints with good wet adhesion.

DETAILED DESCRIPTION OF THE INVENTION

As noted above, the monomers of this invention can be prepared by reacting a diisocyanate of formula OCN—$R^4$—NCO with an ethylenically unsaturated compound of formula HY—$R^6$—Z—C(O)—$CR^8$=$CH_2$ and then reacting the product thereof with a compound of formula II. The conditions of the reaction should be such that the product is essentially monoethylenically unsaturated. This will ensure that the monomer composition will not contain di-ethylenic unsaturation which can cause crosslinking in a polymer subsequently prepared from the monomer composition. The monomers can also be prepared by first reacting the diisocyanate with the compound of formula II and then reacting the product with the ethylenically unsaturated compound. The reaction conditions should likewise be such that the only one of the isocyanate groups reacts with a compound of formula II. This will ensure that the product will consist essentially of mono-ethylenically unsaturated polymerizable materials. Thus, the use of the term "consisting essentially" is intended to exclude compositions which contain significant amounts of di-ethylenic compounds and non-polymerizable compounds.

Examples of the compounds of formula II include the compound N-aminoethylethyleneurea (hereinafter "AEEU"). AEEU is commercially available and can be made as described in U.S. Pat. No. 2,613,212, the disclosure of which is incorporated herein by reference. The other variants of compound II can be made by varying the reactants used in the reaction of U.S. Pat. No. 2,613,212 or by derivatizing the products thereof.

Examples of the ethylenically unsaturated compounds include hydroxyethyl methacrylate, hydroxyethyl acrylate, hydroxypropyl methacrylate, and hydroxypropyl acrylate. These compounds are commercially available and can be made by methacrylating or acrylating the respective ethylene or propylene glycol. The sulfur and amino analogues can be made similarly.

Examples of alicylic diisocyanate compounds include isophorone diisocyanate which is commercially available and which can be prepared by the phosgenation of isophorone diamine. Other alicyclic diisocyanates can be prepared by the phosgenation of the corresponding diamine. It is important that such other alicyclic diisocyanates also show, under the chosen reaction conditions, a sufficient difference in reactivity between the two isocyanate groups to result in an intermediate that is essentially a monourethane, or the sulfur or amino analogue thereof.

A means of providing a difference in reactivity of the isocyanate groups is steric hindrance of one group that is greater than the steric hindrance of the other group, e.g. by alkyl groups pendant to the alicyclic ring. For example, it is believed that in isophorone diisocyanate, wherein one isocyanate group is pendent to an alicyclic ring carbon of said residue and the other isocyanate group is linked to said isocyanate ring through a methylene group, that one of the methyl groups that is pendant to said alicyclic ring in a cis configuration to said methylene group and is pendant to the alicyclic ring that two ring positions away from the ring position of said methylene group, sterically hinders the isocyanate group that is linked to the alicyclic ring through a methylene group.

Each of the reactions is typically carried out in a polar, aprotic organic solvent, e.g. acetonitrile, dimethyl sulfoxide, N-methyl pyrolidone, dimethyl formamide, tetrahydrofuran, dioxane, and di-capped glycol ethers or esters. The molar ratio of alicyclic diisocyanate to ethylenically unsaturated compound will typically be about unity, e.g. about 1.05:1 to about 1:1.05. The reaction is typically performed in the presence of a catalyst, e.g. dibutyl tin dilaurate (DBTL). The reaction medium for the reaction of the alicyclic diisocyanate and the ethylenically unsaturated compound is typically maintained at a temperature between about 25° C. to about 90° C., more typically from about 30° C. to about 70° C., and most typically from about 40° C. to about 60° C. The reaction medium of the product of the first reaction with the compound of formula II is typically maintained at ambient temperature.

The selection of catalyst and reaction temperature may have a great effect on the difference in reactivity of the two isocyanate groups of the alicyclic diisocyanate. In particular, the use of DBTL and lower reaction temperatures should increase the difference in reactivity, compared with an uncatalyzed reaction at higher temperatures.

The product will typically be a mono-urethane with essentially no di-ethylenically unsaturated products. This is important because di-ethylenically unsaturated products will typically act as cross-linkers in subsequent polymerization reactions and cross-linkers may have one or more detrimental effects, e.g. may cause the formation of coagulum in a latex of the polymer. If the compound of formula II is reacted first with the diisocyanate, it is important that the product be a monourethane so that the ultimate product will contain essentially no non-polymerizable compounds which can be leached from a coating made from a polymer formed from the monomer. Thus, preferred compositions will have been prepared from an intermediate that has less di-ethylenic products and less non-polymerizable product than a composition prepared from the same reactants without the use of a catalyst at a temperature of 80° C.

The compounds of formula I are ethylenically unsaturated and, thus, are polymerizable through this unsaturation. The monomer may be useful in a variety of homopolymers and copolymers, e.g. those produced by solution polymerization, but should be most useful as a comonomer in the production of latices through emulsion polymerization. Emulsion polymerization is discussed in G. Pohlein, "Emulsion Polymerization", *Encyclopedia of Polymer Science and Engineering,* vol. 6, pp. 1–51 (John Wiley & Sons, Inc., N.Y., N.Y., 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox intiators. The product, a colloidal dispersion of the polymer or polymer solution, is called a latex.

The comonomers which are typically employed include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof.

In the above process, suitable initiators, reducing agents, catalysts and surfactants are well-known in the art of emulsion polymerization. Typical initiators include hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Suitable surfactants include ionic and nonionic surfactants such as alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; an alkali metal or an ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

A typical process of emulsion polymerization preferably involves charging water to a reactor and feeding as separate streams a pre-emulsion of the monomers and a solution of the initiator. A small amount of the pre-emulsion and a portion of the initiator may be charged initially at the reaction temperature to produce a "seed" latex. The "seed" latex procedure results in better particle-size reproducibility. Normally the pre-emulsion and the initiator solution are fed into the reactor over a period of time such that at any given time during the synthesis the conversion of monomers to polymers is essentially complete. The advantages of adding the ingredients in this manner are better compositional control of copolymers and better temperature control of the polymerization. Under "normal" initiation conditions, that is initiation conditions under which the initiator is activated by heat, the polymerization is normally carried out at 75–85° C. A typical "normal" initiated process, for example, could employ ammonium persulfate as initiator at a reaction temperature of 80±2° C. Under "redox" initiation conditions, that is initiation conditions under which the initiator is activated by a reducing agent, the polymerization is normally carried out at 60–70° C. Normally, the reducing agent is added as a separate solution. A typical "redox" initiated process, for example, could employ potassium persulfate as the initiator and sodium metabisulfide as the reducing agent at a reaction temperature of 65±2° C.

In the above emulsions, the polymer preferably exists as a generally spherical particle, dispersed in water, with a diameter of about 50 nanometers to about 500 nanometers. Gel content can be determined using the method taught in U.S. Pat. No. 5,371,148, incorporated herein by reference. Glass transition temperature (Tg) is a calculated number based on the proportion of each monomer utilized and the corresponding Tg for a homopolymer of such a monomer.

In addition to making emulsion polymers, it is contemplated that the reaction products and compounds of the present invention be used to form solution copolymers.

In particular, the reaction products and compounds of this invention may be incorporated in effective amounts in aqueous polymer systems to enhance the wet adhesion of paints made from the polymers. The commonly used monomers in making acrylic paints are butyl acrylate, methyl methacrylate, ethyl acrylate and the like. In acrylic paint compositions the polymer is comprised of one or more esters of acrylic or methacrylic acid, typically a mixture, e.g. about 50/50 by weight, of a high Tg monomer (e.g. methyl methacrylate) and a low Tg monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

The novel reaction products and compounds of this invention may be added to the monomer composition from which acrylic or vinyl-acrylic polymers are formed in a concentration which may vary over a wide range. Preferably, the concentration is at least sufficient to improve the wet adhesion of paints made from the polymer composition. Concentrations may range from about 0.1% to about 4% by weight based on the total weight of monomers. It is preferred that the concentration be from about 0.2% to about 2%.

In certain embodiments, a latex of this invention is blended with a conventional latex to form a blend which will exhibit improved wet adhesion when used as a coating material. In such embodiments, it may be advantageous to use a latex of this invention having a relatively greater percentage of a monomer of this invention, e.g. from about 3% to about 10% by weight, more typically about 4% to about 8% by weight, of the total weight of the monomers.

The latices of this invention will be useful in preparing coating formulations, particularly architectural paints. The formulation of architectural paints is discussed in J. Lowell, "Coatings", *Encyclopedia of Polymer Science and Engineering*, vol. 3, pp. 648–653 (John Wiley & Sons, Inc., N.Y., N.Y., 1985), The formulation of a latex paint comprises pigment and latex as the basic functional ingredients. Among the various additives that are also typically used are: dispersing agents, (e.g. tetrasodium pyrophosphate or soya lecithin), protective colloids and thickeners (e.g. sodium salts of carboxyl-functional acrylic polymers, hydroxyethylcellulose, carboxymethylcellulose, colloidal clay, or gum arabic), defoamers (e.g. tri-n-butyl phosphate, or n-octyl alcohol), coalescing agents (hexylene glycol or ethylene glycol monobutyl ether), flatting agents, freeze-thaw additives (e.g. ethylene glycol), biocides (e.g. mercury, copper or phenolics), pH control agents (e.g. ammonium hydroxide), and UV absorbers and/or stabilizers.

Pigment compositions used in interior and exterior house paints usually comprise hiding white pigments, other tints and colors ordinarily being obtained by mixing other colored paint pigments with the white pigments. Any of the inorganic and organic pigments, pigment lakes, insoluble dyes and other durable coloring matter ordinarily used in formulating durable exterior paints, varnishes, enamels and lacquers can be used in pigmenting the invention paint compositions. Thus, the pigments suitable for use in the coating compositions envisioned by the present invention are the typical organic and inorganic pigments, well-known to one of ordinary skill in the art of surface coatings, especially those set forth by the Colour Index, 3d Ed., 2d Rev., 1982, published by the Society of Dyers and Colourists in association with the American Association of Textile Chemists and Colorists. Examples include, but are not limited to the following: CI Pigment White 6 (titanium dioxide); CI Pigment Red 101 (red iron Oxide); CI Pigment Yellow 42, CI Pigment Blue 15, 15:1, 15:2, 15:3, 15:4 (copper phthalocyanines); CI Pigment Red 49:1; and CI Pigment Red 57:1.

Typical useful white hiding pigments are: rutile titanium dioxide, anatase titanium dioxide, zinc oxide, leaded zinc oxide, zinc sulfide, lead titanate, antimony oxide, zirconium oxide, white lead, basic lead silicate, lithopone, titanated lithopone, titanium-barium pigment, titanium-calcium pigment and titanium-magnesium pigment. The titanium dioxide pigments ordinarily are preferred.

While the indicated pigmentation can be solely of hiding prime pigments, it is economically impractical to use solely prime pigments at the indicated high pigment volume concentration. As is ordinary practice in paint formulation, the total pigment usually consists of hiding prime pigments extended with well-known pigment extenders such as calcium carbonate, gilders whiting talc, barytes, magnesium silicates, aluminum silicates, diatomaceous earth, china clay, asbetine, silica and mica. The relative proportions of the prime white pigment and the pigment extender in the pigment mixture may be varied widely, but usually the hiding prime pigments is present at a pigment volume concentration which provides the desired paint covering power or hiding and the extender pigment is present in an amount which provides the paint with the desired total pigment volume concentration. Prime pigments and extender pigments range widely in density, but ordinarily white house paints and light tints thereof have a pigment composition whereof the extender pigment is present in the weight proportion of 0.4 to 4 parts per part of hiding prime pigment. Pigments can be dispersed in the aqueous paint vehicle by any of the well-known techniques of pigment dispersion in paint formulation, such as roller milling, ball or pebble grinding, sand grinding as described in Hochberg U.S. Pat. No. 2,581,414, paddle-mixer dispersion techniques, Werner-Pfleiderer "dough" mixer mixing and other pigment paste techniques. The pigments the aqueous dispersion polymer composition of this invention or the pigments can be wet and dispersed in a separate aqueous slurry in the absence of the aqueous dispersion polymer and then combined by simple mixing. The order of combining the pigments is not significantly critical.

The pigment composition is preferably dispersed in the presence of a water-soluble and swellable colloidal bodying agent and an auxiliary surfactant in addition to the surfactants present in the respective latices to stabilize the polymer dispersions. The auxiliary surfactant for dispersing the pigment composition can be non-ionic, anionic, or cationic, preferably of the water-soluble type. The selection of this dispersing surfactant is judicious to provide compatibility and non-reactivity with the dispersion stabilizing surfactants of the aqueous polymer dispersion of the paint vehicle. The surfactant for dispersing the pigment composition may be the same or different from the stabilizing surfactants of the dispersion. Examples of dispersing agents and surfactants include sulfosuccinnates, sulfated ethoxylated nonylphenol, 2-amino-2-methyl-1-propanol, and the like.

Ordinarily a concentration of up to 2% of the auxiliary pigment-dispersing surfactant based on the weight of the pigment composition is adequate, the preferred concentration being 0.1% to 1% on the indicated basis. It is preferred that the total amount of pigment dispersing surfactant and the stabilizing surfactants of the dispersion does not exceed 10% based on the total weight of the latex polymer.

Examples of viscosity, suspension, and flow control agents include COLLOID TM brand dispersants of Rhodia Inc., polyaminoamide phosphate, high molecular weight carboxylic acid salts of polyamine amides, and alkylene amine salts of an unsaturated fatty acid, all available from BYK Chemie U.S.A. under the trademark ANTI TERRA Registered TM. Further examples include polysiloxane copolymers, polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide. Other examples of thickeners includes the methane/ethylene oxide associative thickeners and water soluble carboxylated thickeners, for example, those sold under the UCAR POLYPHOBE trademark by Union Carbide.

The viscosity of the aqueous dispersion paint composition also can be varied widely. A stormer viscosity of about 70 to 100 K.U. at 25° C. is a desirable ready-to-apply brush consistency. This is not a critical characteristic as the paint can be further modified satisfactorily with thixotropy controlling agents to provide the composition with non-drip characteristics with adequate brushout characteristics.

Examples of flatting agents include synthetic silica, available from the Davison Chemical Division of W. R. Grace & Company under the trademark SYLOID Registered TM; polypropylene, available from Hercules Inc., under the trademark HERCOFLAT Registered TM; synthetic silicate, available from J. M. Huber Corporation under the trademark ZEOLEX Registered TM.

Several proprietary antifoaming agents are commercially available, for example, under the trademark COLLOID™ of Rhodia Inc., BRUBREAK of Buckman Laboratories Inc., under the BYK Registered TM trademark of BYK Chemie, U.S.A., under the FOAMASTER Registered TM and NOPCO Registered TM trademark of Henkel Corp./Coating Chemicals, under the DREWPLUS Registered TM trademark of the Drew Industrial Division of Ashland Chemical Company, under the TROYSOL Registered TM and TROYKYD Registered TM trademarks of Troy Chemical Corporation, and under the SAG Registered TM trademark of Union Carbide corporation.

Examples of fungicides, mildewcides, and biocides include 4,4-dimethyloxazolidine, 3,4,4-trimethyloxazolidine, modified barium metaborate, potassium N-hydroxy-methyl-N-methyldithiocarbamate, 2-(thiocyanomethylthio) benzothiazole, potassium dimethyl dithiocarbamate, adamantane, N-(trichloromethylthio) phthalimide, 2,4,5,6-tetrachloroisophthalonitrile, orthophenyl phenol, 2,4,5-trichlorophenol, dehydroacetic acid, copper naphthenate, copper octoate, organic arsenic, tributyl tin oxide, zinc naphthenate, and copper 8-quinolinate.

Examples of U.V. absorbers and U.V. light stabilizers include substituted benzophenone, substituted benzotriazoles, hindered amines, and hindered benzoates, available from American Cyanamid Company under the trademark CYASORB UV, and diethyl-3-acetyl-4-hydroxy-benzyl-phosphonate, 4-dodecyloxy-2-hydroxy benzophenone, and resorcinol monobenzoate.

Such paint or coating additives as described above form a relatively minor proportion of the coating composition, preferably about 0.05 weight % to about 5.00 weight %.

As a further aspect of the present invention, there is provided a coating composition optionally containing one or more of the above-described additives. It may also be desirable to utilize a water-miscible organic solvent. Such solvents are well known and include ethanol, n-propanol, isopropanol, n-butanol, sec-butanol, isobutanol, ethylene glycol monobutyl ether, propylene glycol n-butyl ether, propylene glycol methyl ether, propylene glycol monopropyl ether, dipropylene glycol methyl ether, diacetone alcohol, Eastman Chemical Company's TEXANOL Registered TM ester alcohol, and other water-miscible solvents.

While the total non-volatile content of the aqueous dispersion paint composition, ordinarily designated as the solids content, can vary widely, it is desirable that the non-volatile content be at least 30% by weight in order that a practical amount of paint per coat is applied. The aqueous paint can be satisfactorily formulated in a non-volatile content as great as 70%, but at this concentration thinning with water is ordinarily necessary for satisfactory application. The preferred non-volatile content is from about 40% to 60% by weight. The paint may be formualated as a low or zero VOC composition as defined by EPA regulations.

The paints of this invention will be particularly useful when formulated and applied as interior or exterior architectural coatings. Thus, the paints will typically be applied to an architectural substrate, such as primed or unprimed drywall, wood siding or trim, aluminum siding, concrete, stucco, and the like, and then allowed to air dry. The latices of this invention may also be formulated into coatings for industrial coatings, textile coatings, ink coatings, adhesives, or coatings for plastics.

The following examples will serve to illustrate the invention and should not be construed to limit the invention. All parts, percentages, ratios and the like in the following examples or elsewhere in the disclosure of the invention are by weight unless other wise apparent from the context of their use.

EXAMPLES

Example 1

Synthesis of Wet Adhesion Monomer Composition

A 500 mL round-bottom flask fitted with a condenser, mechanical stirrer, thermometer and addition funnel was charged with 100 parts of acetonitrile, 0.26 parts p-methoxyphenol, 0.69 parts dibutyltin dilaurate as catalyst, and 47.10 parts isophorone diisocyanate. A subsurface air sparge was initiated in the stirring solution. Slow addition of 27.86 parts of hydroxyethyl methacrylate helped raise the solution temperature to 40° C. The temperature was raised and held at 60° C. for 4 hours after the completed alcohol addition. GC analysis of the reaction solution showed the consumption of the starting materials and formation of new compounds. The solution temperature was lowered to ambient prior to the slow addition of 28.20 parts of aminoethylimidazolidinone. Chromatographic and FT-IR analysis of the reaction solution gave no indication that starting materials were evident after one hour. NMR characterization of the product indicated the product to be isomeric mixtures of the desired urea-urethane species.

FTIR provided the following absorptions on a sample of the product from which the acetonitrile was removed by evaporation:

N—H at 3321 $cm^{-1}$

C=O at 1704 $cm^{-1}$

The spectrum did not show any absorption in the 2200–2300 $cm^{-1}$ region indicating the absence of any isocyanate (NCO) groups in the product.

$^{13}$C NMR provided the following results from a sample of the reaction solution:

TABLE 1

$^{13}$ NMR Data for Wet Adhesion Monomer Reaction Product

| Chemical Shift | Peak Type | Assignment |
|---|---|---|
| 18.3 | $CH_3$ | Methacrylate methyl |
| 23.5 | $CH_3$ | IPDI methyl |
| 27.7 | $CH_3$ | IPDI methyl |
| 31.8 | C | IPDI quaternary C |
| 35.1 | $CH_3$ | IPDI methyl |
| 36.6 | $C(CH_3)_2$ | IPDI quaternary C |
| 38.4 | CH | IPDI tertiary C |
| 41.4, 44.0, | $CH_2$ | Ring methylenes |

TABLE 1-continued $^{13}$ NMR Data for Wet Adhesion Monomer Reaction Product

| Chemical Shift | Peak Type | Assignment |
|---|---|---|
| 45.3, 46.2, | | |
| 47.2, 53.7, | | |
| 62.2, 63.2 | | |
| 117.1 | $CH_3$ | Acetonitrile |
| 126.0 | $CH_2=$ | Methacrylate methylene |
| 136.2 | C= | Methacrylate carbon |
| 155.8 | C=O | Carbamate |
| 159.3 | C=O | Urea |
| 163.6 | C=O | Imidazolidinone |
| 167.1 | C=O | Methacrylate |

The use of DBTL promotes enhances the reactivity of the secondary isocyanate group (i.e. the isocyanate group which is directly substituted on the cyclohexyl ring of the IPDI) compared to the primary isocyanate group. Thus, the composition produced by the procedure of this example will be consist essentially of a monomer compound of formula I wherein "Y" is bonded to the residue of the secondary isocyanate group of IPDI.

The wet adhesion monomer was concentrated to 70% by removing acetonitrile using an air sparge at ambient temperature. This 70% active solution was used to prepare the latexes described in the subsequent examples.

Example 2

Latex Synthesis with Wet Adhesion Monomer Composition

An all acrylic emulsion polymer, for paint application, containing 1.4% (BOTM) of the product of Example 1, was prepared using the following ingredients:

TABLE 2

| Ingredients | Parts by Weight |
|---|---|
| Product of Example 1 | 10.0 |
| (70% by wt. solution) | |
| Methacrylic Acid | 5.0 |
| Methyl Methacrylate | 260.0 |
| Butyl Acrylate | 230.0 |
| Rhodacal DS-4 ® | 21.7 |
| Ammonium Persulfate | 2.0 |
| Ammonium Hydroxide | 3.0 |
| Water, de-ionized | 472.6 |

A one liter reactor was charged with 192 parts of water. The reactor was purged with nitrogen and heated to 82° C. A monomer emulsion was prepared with the monomers and surfactant in 182.6 parts of water. The initiator was delivered as a 2% initiator solution. A seed polymer was prepared by adding 25% of the initiator solution and 2% of the monomer emulsion to the heated reactor. The seed dispersion was allowed to stir for fifteen minutes. Separate streams of the monomer emulsion and the initiator solution were then fed into the reactor over the next 3 hours while maintaining a reaction temperature of 80° C. After the completed addition, the temperature was raised to 85° C. for 0.5 hours. The latex was cooled to ambient temperature and the solution pH adjusted to 8.9 with ammonium hydroxide. The latex was filtered and bottled.

This latex exhibited the following properties:

TABLE 3

| | |
|---|---|
| % coagulum (botl) | 0.20 |
| % solids | 51.0 |
| % conversion | 100 |
| Viscosity | 32 cps @60 rpm |
| Mean Particle Diameter (nm) | 342 |
| Warring Blender Stability (min) | >5 |
| Freeze/thaw Stability (cycles) | >5 |

Comparative Example A
Latex Synthesis without Wet Adhesion Monomer

An all acrylic emulsion polymer, for paint application, containing no wet adhesion monomer was prepared as above using:

TABLE 4

| Ingredients | Parts by Weight |
|---|---|
| Methacrylic Acid | 5.0 |
| Methyl Methacrylate | 265.0 |
| Butyl Acrylate | 230.0 |
| Rhodacal DS-4 ® | 21.75 |
| Ammonium Persulfate | 2.0 |
| Ammonium Hydroxide | 2.6 |
| Water, de-ionized | 472.6 |

A one liter reactor was charged with 192 parts of water. The reactor was purged with nitrogen and heated to 82° C. A monomer emulsion was prepared with the monomers and surfactant in 182.6 parts of water. The initiator was delivered as a 2% initiator solution. A seed polymer was prepared by adding 25% of the initiator solution and 2% of the monomer emulsion to the heated reactor. The seed dispersion was allowed to stir for fifteen minutes. Separate streams of the monomer emulsion and the initiator solution were then fed into the reactor over the next 3 hours while maintaining a solution temperature of 80° C. After the completed addition, the temperature was raised to 85° C. for 0.5 hours. The latex was cooled to ambient temperature and the solution pH adjusted to 8.8–9.2 with ammonium hydroxide. The latex was filtered and bottled.

This latex exhibited the following properties:

TABLE 5

| | |
|---|---|
| % coagulum (botl) | 0.09 |
| % solids | 50.8 |
| % conversion | 99.95 |
| Viscosity | 25 cps @60 rpm |
| Mean Particle Diameter (nm) | 342 |
| Warring Blender Stability (min) | >5 |
| Freeze/thaw Stability (cycles) | 3 |

Example 3 and Comparative Example B
Wet Adhesion Evaluation
Preparation of a Semi-Gloss Paint A pigment dispersion was prepared with the following materials:

TABLE 6

| Pigment Phase Materials | Parts by Weight |
|---|---|
| Water | 37.70 |
| Bentonite Clay (Bentone LT, Rheox, Inc.) | 0.90 |
| Defoamer (Colloid 643, Rhodia Inc.) | 0.20 |
| Biocide (Nuocept 95, Huls America) | 0.60 |
| Potassium Tripolyphosphate | 0.20 |
| Acrylic Dispersant (Colloid 225, Rhodia Inc.) | 1.00 |
| Surfactant (Antarox BL-225, Rhodia Inc.) | 0.50 |
| Propylene Glycol | 3.50 |
| $TiO_2$ Pigment (Kronos 2020, Kronos) | 55.40 |
| Sub-Total | 100.00 |

These ingredients were mixed in a high speed dispersing mixer until smooth. The pigment phase was then mixed (i.e. let-down) with the following materials to make a semi-gloss paint:

TABLE 7

| Let-Down Materials | Parts by Weight |
|---|---|
| Latex of Example 2 or Comparative Example A | 98.7 |
| Water | 11.15 |
| Propylene Glycol | 3.5 |
| Ammonium Hydroxide | 0.4 |
| Defoamer (Colloid 643) | 0.2 |
| Coalescent (Texanol, Eastman Chemicals) | 3.15 |
| Sub-Total | 117.1 |

Total Paint Weight 217.1

SCRUB TEST

The paint was then evaluated for wet scrub properties using a modified ASTM-D 2486-69 Latex Paint Scrub Test. The test involved a 3 mil drawdown of high gloss, oil based, enamel made on the full length of a Leneta Chart and air-dried a minimum of seven days at room temperature. This painted strip was then covered with a perpendicular 3 mil drawdown of a control paint and also the test paint. The latex paints were allowed to air dry for two days at room temperature.

The Leneta chart was fastened to the glass plate of a Gardner Scrub tester. The scrub brush was soaked in an aqueous solution of 2% Igepal CO-630 for a minimum of 30 minutes then shaken vigorously to remove excess detergent solution. Ten grams of Leneta standardized scrubbing medium were spread over the brush bristles. The brush was then mounted in the holder of the Gardner scrub tester and the panel wetted with 5 parts water. After each 250 cycles, before failure, another 10 parts of the scrub media was added to the brush, the brush remounted, and an additional 5 parts water was placed on the panel in the path of the brush before continuing the test. The number of cycles before failure was noted. A failure was defined as complete erosion of the test paint across the entire width of the drawdown.

Results

The paint of Example 3, which included the wet adhesion monomer, survived more than 2,000 cycles of this wet scrub test. A similar paint without the wet adhesion monomer modified latex failed the scrub test after 154 cycles.

Examples 4–7

Example 2 was repeated as Examples 4 and 5, but with levels of the wet adhesion monomer of Example 1 at 0.5% and 1.0% respectively. Example 3 was then twice repeated as Examples 6 and 7 and each of the paints made therefrom survived more than 2,000 cycles of the wet scrub test.

What is claimed is:

1. A composition of matter consisting essentially of a monomer having the formula:

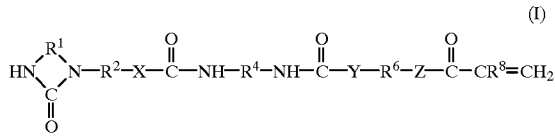

(I)

wherein:
$R^1$ is alkylene having about 2 or 3 carbon atoms;
$R^2$ is alkylene having about 2 to about 10 carbon atoms;
X is oxygen, sulfur, or $NR^3$ wherein $R^3$ is hydrogen, alkyl, alicyclic, aryl, heteroalkyl, heterocyclic;
$R^4$ has the structure of the residue of an alicylic diisocyanate wherein the isocyanate groups have reactivites that differ one from another;
Y is oxygen, sulfur, or $NR^5$ wherein $R^5$ is hydrogen, alkyl, alicyclic, aryl, heteroalkyl, or heterocyclic;
$R^6$ is alkylene, arylene, aralkylene, alkarylene, or heteroalkylene;
Z is oxygen, sulfur, or $NR^7$ wherein $R^7$ is hydrogen, alkyl, alicyclic, aryl, heteroalkyl, or heterocyclic; and
$R^8$ is hydrogen or methyl.

2. The composition of claim 1 wherein $R^4$ has the structure of the residue of an alicylic diisocyanate wherein one or more alkyl groups pendant to an alicylic provide greater steric hindrance to one isocyanate group than the other isocyanate group.

3. The composition of claim 1 wherein $R^4$ has the structure of the residue of isophorone diisocyanate.

4. The composition of claim 1 wherein $R^8$ is methyl.

5. The composition of claim 1 wherein $R^3$ is hydrogen.

6. The composition of claim 1 wherein $R^1$ is ethylene.

7. The composition of claim 1 wherein $R^2$ is ethylene or propylene.

8. The composition of claim 1 wherein X is oxygen.

9. The composition of claim 1 wherein $R^6$ is ethylene or propylene.

10. The composition of claim 1 wherein Y and Z are both oxygen.

11. The composition of claim 1 wherein $R^3$ is hydrogen and $R^8$ is methyl.

12. The composition of claim 1 wherein $R^1$ and $R^2$ are ethylene and X is NH.

13. The composition of claim 1 wherein Y and Z are both oxygen, $R^6$ is ethylene, and $R^8$ is methyl.

14. The composition of claim 1 wherein X is NH, $R^8$ is methyl and $R^4$ has the structure of the residue of an alicylic diisocyanate wherein one or more alkyl groups pendant to an alicylic ring provide greater steric hindrance to one isocyanate group than the other isocyanate group.

15. The composition of claim 14 wherein $R^4$ has the structure of the residue of isophorone diisocyanate.

16. The composition of claim 15 wherein $R^1$ and $R^2$ are ethylene, Y and Z are both oxygen, and $R^6$ is ethylene.

17. The composition of claim 16 wherein Y is bonded to the residue of the secondary isocyanate group of said isophorone diisocyanate.

18. A method of making a composition as claimed in claim 1 wherein a diisocyanate of formula OCN—$R^4$—NCO is reacted with a compound of formula HY—$R^6$—Z—C(O)—$CR^8$=$CH_2$ and the product thereof is reacted with a compound of formula:

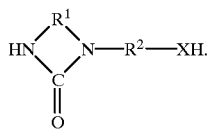

19. The method of claim 18 where $R^4$ has the structure of the residue of an alicylic diisocyanate wherein one or more alkyl groups pendant to an alicylic ring provide greater steric hindrance to one isocyanate group than the other isocyanate group.

20. The method of claim 18 wherein $R^4$ has the structure of the residue of isophorone diisocyanate.

21. The method of claim 18 wherein $R^8$ is methyl.

22. The method of claim 18 wherein $R^8$ is hydrogen.

23. The method of claim 18 wherein $R^1$ is ethylene.

24. The method of claim 18 wherein $R^2$ is ethylene or propylene.

25. The method of claim 18 wherein X is oxygen.

26. The method of claim 18 wherein $R^6$ is ethylene of propylene.

27. The method of claim 18 wherein Y and Z are both oxygen.

28. The method of claim 18 wherein $R^3$ is hydrogen and $R^8$ is methyl.

29. The method of claim 18 wherein $R^1$ and $R^2$ are ethylene and X is NH.

30. The method of claim 18 wherein Y and Z are both oxygen, $R^6$ is ethylene, and $R^8$ is methyl.

31. The method of claim 18 wherein X is NH, $R^8$ is methyl and $R^4$ has the structure of the residue of an alicylic diisocyanate wherein one or more alkyl groups pendant to an alicylic ring provide greater steric hindrance to one isocyanate group than the other isocyanate group.

32. The method of claim 31 wherein $R^4$ has the structure of the residue of isophorone diisocyanate.

33. The method of claim 32 wherein $R^1$ and $R^2$ are ethylene, Y and Z are both oxygen, and $R^6$ is ethylene.

34. The method of claim 33 wherein Y is reacted wiht the secondary isocyanategroup of said isophorone diisocyanate.

* * * * *